US007242978B2

(12) United States Patent
Cao et al.

(10) Patent No.: US 7,242,978 B2
(45) Date of Patent: Jul. 10, 2007

(54) METHOD AND APPARATUS FOR GENERATING A TEMPLATE FOR ARRHYTHMIA DETECTION AND ELECTROGRAM MORPHOLOGY CLASSIFICATION

(75) Inventors: Jian Cao, Shoreview, MN (US); Jeffrey M. Gillberg, Coon Rapids, MN (US); Chris J. Gennaro, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 145 days.

(21) Appl. No.: 11/002,482

(22) Filed: Dec. 2, 2004

(65) Prior Publication Data
US 2005/0137485 A1    Jun. 23, 2005

Related U.S. Application Data

(60) Provisional application No. 60/526,562, filed on Dec. 3, 2003.

(51) Int. Cl.
*A61B 5/04* (2006.01)
*A61N 1/00* (2006.01)

(52) U.S. Cl. .................. 600/518; 600/509; 600/513; 600/515; 600/518; 607/4; 607/5; 607/6; 607/14; 607/25; 607/27

(58) Field of Classification Search .............. 600/509, 600/513, 515, 518; 607/4–6, 25, 27, 14
See application file for complete search history.

(56) References Cited

U.S. PATENT DOCUMENTS

| 3,978,856 A | 9/1976 | Michel ................... 128/2.06 A |
| 4,316,472 A | 2/1982 | Mirowski et al. ........ 128/419 D |
| 4,375,817 A | 3/1983 | Engle et al. ............ 128/419 D |
| 4,384,585 A | 5/1983 | Zipes .................... 128/419 D |
| 4,552,154 A | 11/1985 | Hartlaub .................... 128/702 |
| 4,577,633 A | 3/1986 | Berkovits et al. ..... 128/419 PG |
| 4,587,970 A | 5/1986 | Holley et al. ......... 128/419 PG |
| 4,726,380 A | 2/1988 | Vollmann et al. ..... 128/419 PG |
| 4,727,877 A | 3/1988 | Kallok ................... 128/419 D |
| 4,800,883 A | 1/1989 | Winstrom ............... 128/419 D |
| 4,830,006 A | 5/1989 | Haluska et al. ....... 128/419 PG |

(Continued)

OTHER PUBLICATIONS

Anderson, MH et al., "Performance of Basic Ventricular Tachycardia Detection Algorithms in Implantable Cardioverter Defibrillators: Implications for Device Programming," *PACE*, vol. 20, p. 2975-2983 (1997).

(Continued)

*Primary Examiner*—Carl Layno
*Assistant Examiner*—Natasha Patel
(74) *Attorney, Agent, or Firm*—Michael C. Soldner; Girma Wolde-Michael

(57) ABSTRACT

An implantable medical device and associated method for automatically generating morphology templates during fast cardiac rhythms, confirming a provisional template as a confirmed template, and using the confirmed template to classify subsequent detected arrhythmias. A provisional SVT template may be created during a fast ventricular rate and activated as a confirmed SVT template upon verification that the fast rate was due to an SVT. The confirmed SVT template may be used to discriminate SVT from VT/VF.

10 Claims, 7 Drawing Sheets

U.S. PATENT DOCUMENTS

| | | | | |
|---|---|---|---|---|
| 4,880,005 | A | 11/1989 | Pless et al. | 128/419 PG |
| 4,949,719 | A | 8/1990 | Pless et al. | 128/419 D |
| 4,953,551 | A | 9/1990 | Mehra et al. | 128/419 D |
| 5,117,824 | A | 6/1992 | Keimel et al. | 128/419 D |
| 5,163,427 | A | 11/1992 | Keimel | 128/419 D |
| 5,188,105 | A | 2/1993 | Keimel | 128/419 D |
| 5,261,400 | A | 11/1993 | Bardy | 607/5 |
| 5,273,049 | A | 12/1993 | Steinhaus et al. | 128/696 |
| 5,312,441 | A | 5/1994 | Mader et al. | 607/5 |
| 5,411,524 | A | 5/1995 | Rahul | 607/4 |
| 5,447,519 | A | 9/1995 | Peterson | 607/5 |
| 5,545,186 | A | 8/1996 | Olson et al. | 607/14 |
| 5,718,242 | A | 2/1998 | McClure et al. | 128/704 |
| 5,722,999 | A | 3/1998 | Snell | 607/32 |
| 5,755,736 | A | 5/1998 | Gillberg et al. | 607/4 |
| 5,833,623 | A | 11/1998 | Mann et al. | 600/523 |
| 5,857,977 | A | 1/1999 | Caswell et al. | 600/518 |
| 5,991,656 | A | 11/1999 | Olson et al. | 607/4 |
| 6,091,988 | A | 7/2000 | Warman et al. | 607/5 |
| 6,223,078 | B1 * | 4/2001 | Marcovecchio | 607/5 |
| 6,312,388 | B1 * | 11/2001 | Marcovecchio et al. | 600/508 |
| 6,393,316 | B1 | 5/2002 | Gillberg et al. | 600/515 |
| 6,473,638 | B2 | 10/2002 | Ferek-Petric | 600/523 |
| 6,583,796 | B2 | 6/2003 | Jamar et al. | 345/804 |
| 6,745,068 | B2 * | 6/2004 | Koyrakh et al. | 600/515 |
| 2002/0008791 | A1 | 1/2002 | Okamori et al. | 349/5 |
| 2002/0183637 | A1 | 12/2002 | Kim et al. | 600/510 |
| 2002/0183640 | A1 | 12/2002 | Bjorling | 600/517 |
| 2002/0193695 | A1 | 12/2002 | Koyrakh et al. | 600/510 |

OTHER PUBLICATIONS

Duru, F. et al., "Morphology Discriminator Feature for Enhanced Ventricular Tachycardia Discrimination in Implantable Cardioverter Defibrillators," *PACE*, vol. 23, p. 1365-1374 (2000).

Gillberg, J.M. et al., "Stability of Far-Field Electrogram Morphology During Baseline Rhythm in Patients with Implantable Cardioverter Defibrillators," *PACE*, vol. 23, p. 606 (abstract) (2000).

Gold, MR et al., "Advanced Rhythm Discrimination for Implantable Cardioverter Defibrillators Using Electrogram Vector Timing and Correlation," *J of Cardio Electrophysiology*, vol. 13, No. 11, p. 1092-1097 (Nov. 2002).

Gold, M.R. et al., "A New Defibrillator Discrimination Algorithm Utilizing Electrogram Morphology Analysis," *PACE*, vol. 22, p. 179-182 (1999).

Olson et al., "Onset and Stability for Ventricular Tachyarrhythmia Detection in an Implantable Pacer-Cardioverter-Defibrillator," *Computers in Cardiology*, IEEE Computer Society Press, p. 167-170 (Oct. 7-10, 1986).

Swerdlow, CD et al., "Discrimination of Ventricular Tachycardia from Supraventricular Tachycardia by a Downlanted Wavelet-Transform Morphology Algorithm: A Paradigm for Development of Implantable Cardioverter Defibrillator Detection Algorithms," *J of Cardio Electrophysiology*, vol. 13, No. 5, p. 432-441 (May 2002).

Trivedi, A. et al., "Changes in Ventricular Electrogram Morphology Following ICD Insertion," *PACE*, vol. 23, p. 629 (abstract) (2000).

U.S. Appl. No. 10/826,618, filed Apr. 16, 2004, to Jian Cao et al, entitled "Automated Template Generation Algorithm for Implantable Device".

* cited by examiner

METHOD AND APPARATUS FOR GENERATING A TEMPLATE FOR ARRHYTHMIA DETECTION AND ELECTROGRAM MORPHOLOGY CLASSIFICATION

RELATED APPLICATION

The present invention claims priority and other benefits from U.S. Provisional Patent Application Ser. No. 60/526,562, filed Dec. 3, 2003, entitled "METHOD AND APPARATUS FOR GENERATING A TEMPLATE FOR ARRHYTHMIA DETECTION AND ELECTROGRAM MORPHOLOGY CLASSIFICATION", incorporated herein by reference in its entirety.

FIELD OF THE INVENTION

The present invention relates generally to implantable cardioverter defibrillator devices (ICDs) and, more particularly, to an ICD system and associated methods for creating morphology templates for use in discriminating supraventricular tachycardia (SVT) from ventricular tachycardia and for reporting morphology-related information with stored arrhythmia episode data.

BACKGROUND OF THE INVENTION

Implantable cardioversion/defibrillation devices detect cardiac arrhythmias and deliver electrical pulses to the heart to treat the arrhythmia. The type of electrical stimulation therapy delivered depends on the type of arrhythmia detected. For example, ventricular fibrillation (VF) is a life-threatening condition and is treated immediately by delivering a high-energy defibrillation shock. Ventricular tachycardia (VT), though not immediately life threatening, is a serious condition typically treated first with anti-tachycardia pacing therapies and, if not successful, progressing to more aggressive therapies including high-energy cardioversion shocks if necessary. Atrial arrhythmias, which are sometimes conducted to the ventricles and are then referred to as "supraventricular tachycardias" or "SVTs," are treated by delivering an appropriate anti-tachycardia pacing therapy or cardioversion/defibrillation shock to the atria.

Cardioversion/defibrillation shocks consume large amounts of battery energy and are painful to the patient. One challenge in the design of ICDs is accurately classifying a detected arrhythmia to thereby avoid unnecessary electrical shocks in the ventricle in response to SVTs. Studies have shown that SVTs may occur in up to 30% of ICD patients. In theory, the shape of the QRS complex in the EGM signal during SVT will not change significantly from the QRS complex during normal sinus rhythm (NSR) because ventricular depolarizations are caused by normal HIS-Purkinje conduction from the atrium to the ventricle. If high ventricular rates are due to a ventricular tachycardia (VT), one can expect a very different morphology of the electrogram (EGM) signal of the ventricular depolarization (QRS complex) because of a different pattern of electrical activity of the heart during VT.

One approach to accurately classifying arrhythmias includes examining the morphology of the QRS complex to discriminate normally conducted ventricular beats from abnormal ones based on the similarity of the EGM signal to a sample waveform recorded from the normal heartbeat. A reference template may be generated from a digitized sample waveform and comparisons made between a QRS complex during an unknown rhythm to a QRS template generated during a known rhythm, such as during NSR.

A number of patents describe the use of morphology analysis or template matching in arrhythmia detection and classification. Reference is made, for example, to U.S. Pat. No. 3,978,856 issued to Michel, U.S. Pat. No. 4,552,154 issued to Hartlaub, U.S. Pat. No. 5,273,049 issued to Steinhaus et al., U.S. Pat. No. 5,857,977 issued to Caswell et al., U.S. Pat. No. 5,447,519 issued to Peterson, and U.S. Pat. No. 5,718,242 issued to McClure et al.

One approach for morphology analysis is Correlation Waveform Analysis (CWA) or its less computationally costly counterpart, so-called Area of Difference Analysis (AD). Both require minimization of a function describing differences between two signals (sum of squared differences of wave data points for the case of CWA, and the sum of absolute values of the differences for AD). However such computations as typically performed are more computationally costly and require more power than is generally desirable within implantable ICDs. In U.S. Pat. No. 6,393,316 issued to Gillberg et al., incorporated herein by reference in its entirety, a method and apparatus for reliable discrimination between ventricular depolarizations resulting from normal and abnormal propagation of depolarization wavefronts by means of a wavelet transform based method of depolarization morphology analysis are generally disclosed.

One limitation that is encountered when comparing the morphology of a QRS waveform during an unknown rhythm to a NSR reference template is that the digitized QRS morphology may be altered due to a high ventricular rate associated with an SVT even though a true ventricular arrhythmia is not present. Therefore, in some instances, a fast ventricular rhythm due to an SVT may be incorrectly classified as VT or VF as the result of a mismatch between the depolarization waveform morphology during the fast ventricular rate and a NSR morphology template. It would be desirable therefore to provide a template of a ventricular depolarization waveform during a fast rate due to an SVT to allow morphology comparisons to be made during an unknown rhythm to an SVT morphology template. However, it is challenging to obtain an SVT morphology template in that the acquisition of the template must occur during a known SVT episode and inducing such episodes may be undesirable or impractical. EGM data storage during arrhythmia episodes allows a physician to identify SVT episodes from which a template might be generated. However, sorting through stored arrhythmia episode data to select an episode that best represents the EGM morphology during an SVT can become an arduous task for a physician.

DETAILED DESCRIPTION OF THE PREFERRED EMBODIMENTS

Figure 1:
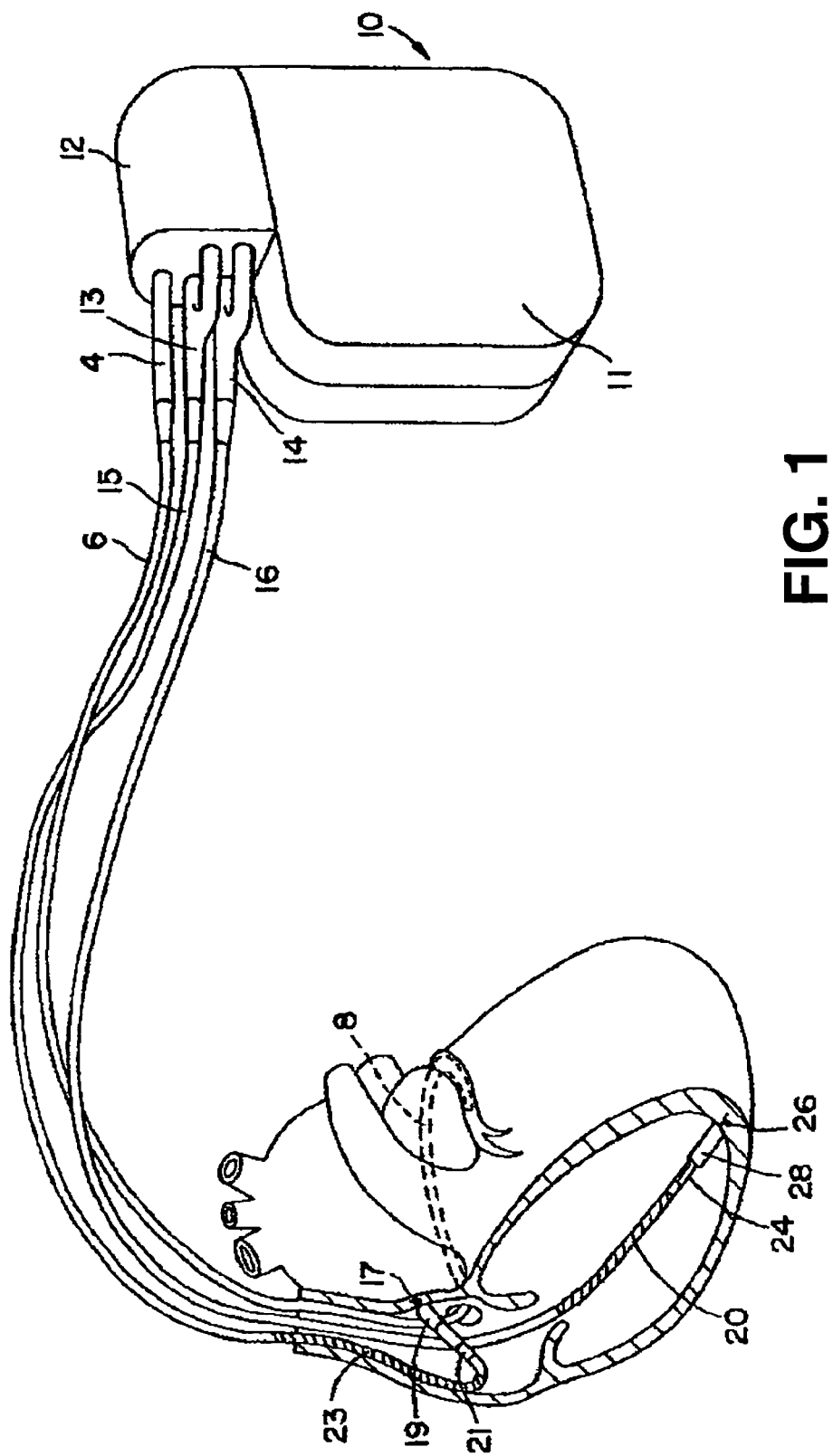
FIG. 1 is an illustration of an implantable pacemaker cardioverter defibrillator device (ICD) coupled to a patient's heart by way of three leads.

The present invention addresses the above-described needs by providing an implantable cardioverter defibrillator (ICD) system and associated methods for automatically generating morphology templates during fast ventricular rhythms, selecting a verified morphology template as an SVT morphology template, using the SVT morphology template during arrhythmia detection and classification methods; and generating reports of EGM morphology-related information in episode summary data stored by the implanted device.

In one aspect of the present invention, a method is provided for creating a provisional SVT template by obtaining a number of EGM morphology waveforms during a fast ventricular rate and deriving a provisional template from the EGM morphology waveforms. The provisional template may be confirmed as an SVT template by a clinician upon review of arrhythmia episode data.

In another aspect of the present invention, confirmation of a provisional template as an SVT template may include a retrospective classification method wherein stored arrhythmia episode data is analyzed using the provisional SVT template to verify correct classification of stored episodes based on comparisons between stored EGM waveforms and the provisional SVT template. If correct classifications are made, the provisional SVT template is confirmed as an SVT template; if incorrect classifications are made, a different provisional SVT template may be selected and confirmed as an SVT template.

In yet another aspect of the present invention, morphology-related information is included in arrhythmia episode data stored in the implanted device for retrieval and display by an external device. In a graphical user interface (GUI), morphology-related information is displayed and may include a label indicating episodes for which provisional morphology templates have been created which may be in the form of a morphology index which allows a clinician to quickly recognize episodes having substantially equivalent EGM morphologies. Other morphology-related information may include a metric of the degree of EGM waveform matching between EGM waveforms used in creating a morphology template. Other morphology-related information may include a graphical display of an EGM signal which may be displayed simultaneously with one or more reference morphology templates along with a corresponding match metric computed by comparing the EGM signal to a reference morphology template.

In a method for using a confirmed SVT template in an arrhythmia detection algorithm, a comparative analysis between unknown cardiac cycles and an SVT template are performed. A comparative analysis may additionally be performed between a NSR template and unknown cardiac cycles. A cardiac cycle is classified according to the template that most closely matches the EGM waveform. A rhythm may be classified as an SVT when a required number of cardiac cycles out of a specified number of consecutive cardiac cycles meet template-matching criteria for either the SVT template or the NSR template.

FIG. 1 is an illustration of an implantable pacemaker cardioverter defibrillator device (ICD) 10 coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by a connector 14 at the proximal end of lead 16 for providing electrical connection to the ICD 10.

The right atrial lead 15 is positioned such that its distal end is in the vicinity of the right atrium and the superior vena cava (SVC). Lead 15 is equipped with a ring electrode 21 and tip electrode 17, optionally mounted retractably within electrode head 19, for sensing and pacing in the right atrium. Lead 15 is further equipped with an SVC coil electrode 23 for delivering high-energy shock therapy. The ring electrode 21, tip electrode 17 and the SVC coil electrode 23 are each connected to an insulated conductor within the body of the right atrial lead 15. Each insulated conductor is coupled at its proximal end to a connector carried by a connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with the RV coil electrode 20 and/or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left ventricle and/or left atrium. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may alternatively serve as a subcutaneous defibrillation electrode in combination with one or more of the defibrillation coil electrodes 8, 20 or 23 for defibrillation of the atria or ventricles.

The depicted positions of the leads and electrodes shown in FIG. 1 in or about the right and left heart chambers are approximate and merely exemplary. The present invention may be practiced using alternative lead systems having pace/sense electrodes adapted for placement at pacing or sensing sites in operative relation to the RA, LA, RV and LV. Such systems may include transvenous leads as shown in FIG. 1 or may alternatively include leads having epicardial or subcutaneous electrodes. The implementation may also include a device that does not employ pacing leads as described here to detect and treat arrhythmias. For example, a device implanted subcutaneously or sub-muscularly in a position over the heart such as an axillary location could use non-intracardiac lead based methods of electrical sensing to detect and deliver therapy. While a particular multi-chamber ICD and lead system is illustrated in FIG. 1, methodologies included in the present invention may be adapted for use with other single chamber, dual chamber, or multichamber ICD systems.

Figure 2:
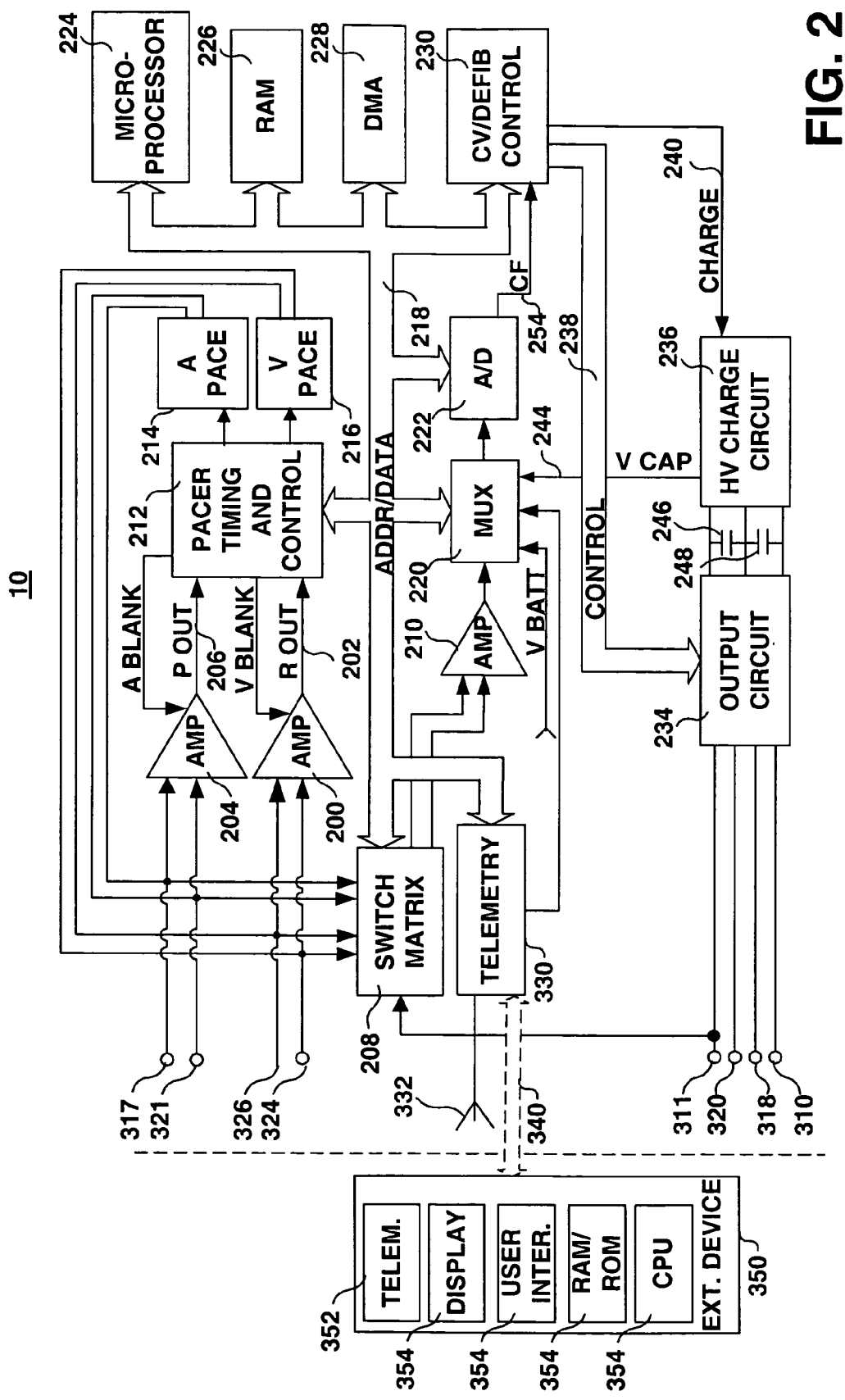
FIG. 2 is a functional block diagram of an ICD system in which the present invention may usefully be practiced.

FIG. 2 is a functional block diagram of an ICD system in which the present invention may usefully be practiced. This diagram should be taken as exemplary of the type of system with which the invention may be embodied and not as limiting, as it is believed that the invention may usefully be practiced in a wide variety of device implementations, including cardioverters and defibrillators which do not provide anti-tachycardia pacing therapies or do not include bradycardia pacing. Methods included in the present invention may also be implemented in monitoring devices, which do not include therapy delivery capabilities. The disclosed embodiment shown in FIG. 2 is a microprocessor-controlled device, but the methods of the present invention may also be practiced with devices employing dedicated integrated circuitry for controlling device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to tip electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the tip electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 employs the digitized EGM signal stored in random access memory 226 in conjunction with morphology analysis methods included in the present invention. For example, the microprocessor 224 may analyze the EGM stored in an interval extending from 100 milliseconds previous to the occurrence of an R-wave detect signal on line 564, until 100 milliseconds following the occurrence of the R-wave detect signal. The operation of the microprocessor 224 in performing the rhythm discrimination methods of the present invention is controlled by software/firmware algorithms resident in microprocessor 224 or stored in associated ROM.

The telemetry circuit 330 receives downlink telemetry from and sends uplink telemetry to an external programmer 350, as is conventional in implantable anti-arrhythmia devices, by means of an antenna 332 via telemetry link 340. Received telemetry is provided to microprocessor 224 via multiplexer 220. Data to be uplinked to the programmer 350 and control signals for the telemetry circuit 330 are provided by microprocessor 224 via address/data bus 218. Data to be uplinked may include a record of detected arrhythmia episodes as is customary in modern ICDs. In accordance with the present invention, a record of detected arrhythmia episodes or events includes morphology-related information determined by the morphology signal analysis methods provided by the present invention. Numerous types of telemetry systems known for use in implantable devices may be used.

The external device 350 may correspond to any external programming device or data retrieval and storage system known for use with implantable medical devices. Generally, external device 350 will include a central processing unit 354 which may include one or more microprocessors; associated RAM and ROM 354; a user interface 354 which may be in the form of a key pad or pointing device; a display which may be an LCD screen for displaying textual and graphical information relating to the programming of device 10 and data retrieved from device 10; and a telemetry circuit 352 to allow telemetric communication with device 10.

The remainder of circuitry included in device 10 illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and/or ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and to diagnose the occurrence of a variety of arrhythmias. In accordance with the present invention, such interval measurements are further used to determine whether minimum rate criteria are met for activation of EGM data storage and morphology analysis. Timeout of an escape interval triggers generation of a pacing pulse by pacer output circuitry 214 or 216. The escape interval counter is also reset by generation of pacing pulse, and thereby controls the basic timing of cardiac pacing function, including anti-tachycardia pacing.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. These calculations include those described in more detail below associated with the arrhythmia discrimination methods included in the present invention.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. Circuitry for controlling the timing and generation of anti-tachycardia pacing pulses as generally described in U.S. Pat. No. 4,577,633 issued to Berkovits et al., U.S. Pat. No. 4,880,005 issued to Pless et al., U.S. Pat. No. 4,726,380 issued to Vollmann et al., and U.S. Pat. No. 4,587,970 issued to Holley et al, all of which patents are incorporated herein by reference in their entireties, may be used.

In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

One embodiment of an appropriate system for delivery and synchronization of ventricular cardioversion and defibrillation pulses and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation pulses and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman, all of which patents are incorporated herein by reference in their entireties. Any known ventricular cardioversion or defibrillation pulse control circuitry may be usable in conjunction with the present invention. For example, circuitry controlling the timing and generation of cardioversion and defibrillation pulses as disclosed in U.S. Pat. No. 4,384,585, issued to Zipes, U.S. Pat. No. 4,949,719, issued to Pless et al., and in U.S. Pat. No. 4,375,817, issued to Engle et al., all incorporated herein by reference in their entireties may be used in a device employing the present invention.

In the illustrated device, delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt. Examples of high-voltage cardioversion or defibrillation output circuitry are generally disclosed in U.S. Pat. No. 4,727,877 issued to Kallok, and U.S. Pat. No. 5,163,427 issued to Keimel, both incorporated herein by reference in their entirety.

Examples of output circuitry for delivery of biphasic pulse regimens may be found in U.S. Pat. No. 5,261,400 issued to Bardy, and U.S. Pat. No. 4,953,551 issued to Mehra et al., incorporated herein by reference in its entirety. An example of circuitry which may be used to control delivery of monophasic pulses is set forth in the above-cited U.S. Pat. No. 5,163,427, to Keimel. However, output control circuitry for generating a multiphasic defibrillation pulse as generally disclosed in U.S. Pat. No. 4,800,883, issued to Winstrom, incorporated herein by reference in its entirety, may also be used in conjunction with a device embodying the present invention.

In modern implantable cardioverter defibrillators, the particular therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. As in the case of currently available ICDs, and as discussed in the above-cited references, it is envisioned that the amplitude of the defibrillation shock may be incremented in response to failure of an initial shock or shocks to terminate fibrillation. Prior art patents illustrating such pre-set therapy menus of anti-tachycardia therapies include the above-cited U.S. Pat. No. 4,726,380 issued to Vollmann et al., above cited U.S. Pat. No. 4,587,970 issued to Holley et al., and U.S. Pat. No. 4,830,006 issued to Haluska, incorporated herein by reference in their entirety.

As discussed above, switch matrix 208 selects which of the various electrodes are coupled to band pass amplifier 210. Amplifier 210 may be a band-pass amplifier, having a band pass extending for approximately 0.5 to 200 hertz. The filtered EGM signal from amplifier 210 is passed through multiplexer 220, and digitized in A-D converter circuitry 222. The digitized EGM data is stored in random access memory 226 under control of direct memory address circuitry 228. Preferably, a portion of random access memory 226 is configured as a looping or buffer memory, which stores at least the preceding several seconds of the EGM signal.

The occurrence of an R-wave detect signal on line 202 is communicated to microprocessor 224 via data/address bus 218, and microprocessor 224 notes the time of its occurrence. If the morphology analysis function is activated, microprocessor 224 may, for example, wait 100 milliseconds or other physician selected interval following the occurrence of the R-wave detect signal, and thereafter transfer the most recent 200 milliseconds or other physician selected interval of digitized EGM stored in the looping or buffer memory portion of the random access memory circuit 226 to a second memory location, where the contents may be digitally analyzed according to the present invention. In this case, the transferred 200 milliseconds of stored EGM will correspond to a time window extending 100 milliseconds on either side of the R-wave detect signal. Window sizes in any case should be sufficient to allow analysis of the entire QRS complexes associated with the detected R-waves. The microprocessor 224 also updates software-defined counters that hold information regarding the R-R intervals previously sensed. The counters are incremented on the occurrence of a measured R-R intervals falling within associated rate ranges. These rate ranges may be defined by the programming stored in the RAM 226.

The following exemplary VT/VF detection method corresponds to that employed in commercially marketed Medtronic implantable pacemaker/cardioverter/defibrillators and employs rate/interval based timing criteria as a basic mechanism for detecting the presence of a tachyarrhythmia. To this end, the device defines a set of rate ranges and associated software-defined counters to track the numbers of intervals falling within the defined ranges.

A first rate range may define a minimum R-R interval used for fibrillation detection, referred to as the "fibrillation detection interval" or "FDI". An associated VF count preferably indicates how many of a first predetermined number of the preceding R-R intervals were less than FDI. A second rate range may include R-R intervals less than a lower tachycardia detection interval "TDI", and an associated VT count (VTEC) is incremented in response to an R-R interval less than TDI but greater then FDI, is not affected by R-R intervals less than FDI, and is reset in response to R-R intervals greater than TDI. Optionally, the device may include a third rate range including R-R intervals greater than the FDI interval, but less than a fast tachycardia detection interval (FTDI) which is intermediate the lower tachycardia detection interval (TDI) and the lower fibrillation detection interval (FDI).

For purposes of the present example, the interval counts may be used to signal detection of an associated arrhythmia (ventricular fibrillation, fast ventricular tachycardia or slow ventricular tachycardia) when they individually or in combination reach a predetermined value, referred to herein as "number of intervals to detect" or "NID". Each rate zone may have its own defined count and NID, for example "VFNID" for fibrillation detection and "VTNID" for ventricular tachycardia detection or combined counts may be employed. These counts, along with other stored information reflective of the previous series of R-R , P-P, P—R, and R—P intervals, such as information regarding the rapidity of onset of the detected short R-R intervals, the stability of the detected R-R intervals, the duration of continued detection of short R-R intervals, the average R-R interval duration and information derived from analysis of stored EMG segments are used to determine whether tachyarrhythmias are present and to distinguish between different types of tachyarrhythmias.

For purposes of illustrating the invention, an exemplary rate/interval based ventricular tachyarrhythmia detection method is described above. Other tachyarrhythmia detection methodologies, including detection methods as described in U.S. Pat. No. 5,991,656, issued to Olson, et al., U.S. Pat. No. 5,755,736, issued to Gillberg, et al., both incorporated herein by reference in their entireties, or other known ventricular and/or atrial tachyarrhythmia detection methods may be substituted. It is believed that the arrhythmia discrimination methods of the present invention may be usefully practiced in conjunction with virtually any underlying rate-based atrial or ventricular tachyarrhythmia detection scheme. Other exemplary detection schemes are described in U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference in its entirety herein. However, other criteria may also be measured and employed in conjunction with the present invention.

For purposes of the present invention, the particular details of implementation of the rate/interval based detection methodologies are not of primary importance. However, it is required that the rate based detection methodologies employed by the device allow identification and detection of rhythms in the rate range in which operation of the morphology analysis function is desired. It is also important that the morphology analysis function be initiated far enough in advance of the point at which a heart rhythm within the desired rate range can be detected to allow for analysis of the required number of waveforms before the heart rhythm is diagnosed positively as being within the desired rate range. In this fashion, the results of the morphology analysis will be available for use immediately in response to the rate or interval based criteria being met. Diagnosis of the detected arrhythmia and a selection of the therapy to be delivered can likewise be done immediately in response to the rate or interval based criteria being met.

For example, the morphology analysis function in conjunction with the above-described detection scheme may be continuously activated, or may appropriately be initiated and analysis of R-wave morphologies begun at the time the VT count equals VTNID minus "n", where "n" is the number of R-waves employed to determine whether the morphology based criterion is met. The same result may also be accomplished by initiating morphology analysis in response to the VT count reaching a different predetermined value substantially less than VTNID.

Figure 3:
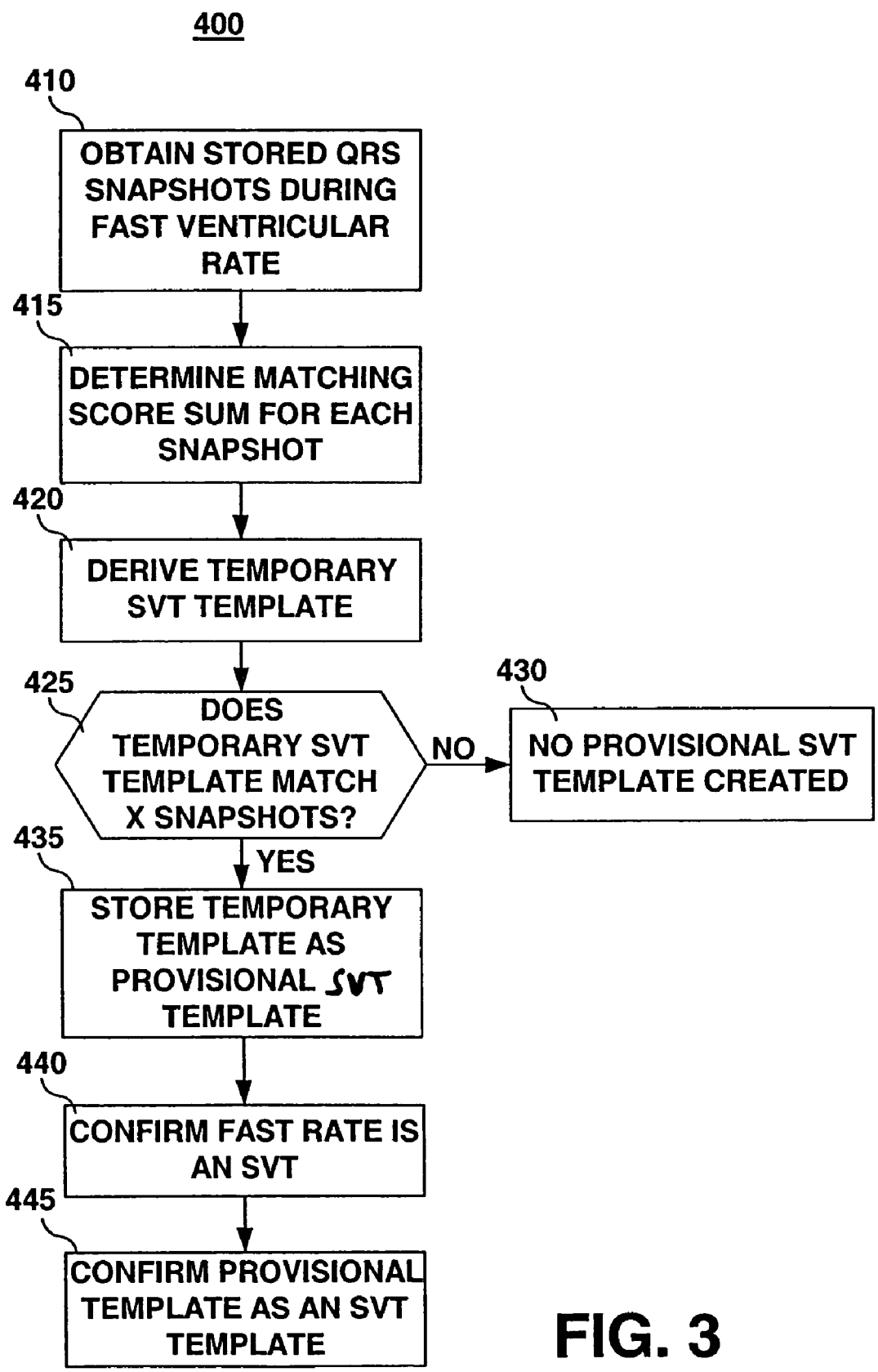
FIG. 3 is a flow chart summarizing steps included in one method for creating a provisional morphology template during a high cardiac rate according to the present invention.

FIG. 3 is a flow chart summarizing steps included in one method for creating a provisional morphology template during a high cardiac rate according to the present invention. Steps included in method 400 for creating a provisional morphology template may be implemented in firmware/hardware resident in implantable device 10 and may be performed automatically during or after an arrhythmia episode detection or upon initiation by a clinician using stored EGM data. Alternatively, method 400 may be implemented in software resident in an external device, such as the programmer 350 shown in FIG. 2 or a personal computer utilizing EMG data retrieved from the implanted device 10. Since EGM waveforms vary between individuals and sensing electrode sites, the methods of the present invention rely on establishing morphology templates for use in arrhythmia detection for each patient.

Aspects of the present invention are expected to be particularly useful in discriminating SVT from VT/VF. As such, method 400 will be described with regard to obtaining a provisional morphology template for use in discriminating SVT from VT/VF. Methods described herein, however, for generating a template during a fast cardiac rate may be adapted for use in atrial arrhythmia classification applications as well. Since the QRS complex during a fast ventricular rate resulting from an SVT may be altered from the QRS complex during normal sinus rhythm, the methods of the present invention rely on establishing a morphology template for a QRS associated with a fast ventricular rate stored as an "SVT template". Establishment of an SVT template for use in arrhythmia discrimination may be in addition to establishing a morphology template for a QRS associated with normal sinus rhythm.

At step 410, QRS snapshots from an EGM signal are stored during a fast ventricular rate. As in an EGM width discrimination method generally described in U.S. Pat. No. 5,312,441 issued to Mader, incorporated herein by reference in its entirety, the methods included in the present invention obtain EGM waveform snapshots derived from the incoming stream of real-time EGM data by centering a morphology window at each sensed event. This technique has been useful for limiting EGM morphology to ventricular depolarizations, allowing the use of far-field EGMs for EGM morphology description and reducing the influence of P-waves and T-waves in the morphological description of the ventricular depolarizations.

The electrodes selected for sensing the EGM for obtaining QRS snapshots may be selected via switch matrix 208 (FIG. 2) and may include electrode sensing configurations corresponding to near-field or far-field EGM signals corresponding to the right and/or left ventricles. In accordance with the methods of the present invention, QRS snapshots are obtained specifically when fast R-R intervals are detected. Such snapshots may be obtained prior to making an arrhythmia detection based on rate-related detection criteria as described above. Upon meeting rate-related criteria which enables morphology analysis methods, QRS snapshots may be stored. For example, a number of QRS snapshots may be obtained that include a number of R-R intervals meeting tachycardia interval detection criteria but have not yet reached VTNID. In one embodiment, eight QRS snapshots are stored corresponding to eight consecutive cardiac cycles leading up to an arrhythmia detection.

QRS snapshots may be stored for each detected arrhythmia episode and retrieved from RAM 226 at step 410 for processing at step 415 within device 100 or off-line by external device 350. At step 415, a matching score sum for each stored QRS snapshot is determined. In order to determine a matching score sum, a morphological comparison is made between a given QRS snapshot and each of the other QRS snapshots stored during or just prior to a single arrhythmia episode. Preferably, the morphological comparison utilizes wavelet transform signal processing methods as disclosed in the above-incorporated U.S. Pat. No. 6,393,316 issued to Gillberg, incorporated herein by reference in its entirety. The wavelet transform method involves computing wavelet transform coefficients for a digitized snapshot and extracting the coefficients that describe the salient features of the waveform. A comparison between the coefficients on one snapshot is compared to the coefficients of another snapshot stored from the same episode to compute a match score. For details regarding computation of a match score, reference is made to the '316 Gillberg patent. Briefly, if the wavelet coefficient numbers match and the coefficients have similar absolute amplitude, then a match weight for the coefficient is added to a match score. A match score is computed for each QRS snapshot when compared to each of the other QRS snapshots stored for a given episode. All of the match scores computed for a QRS snapshot are then summed to determine the match score sum at step 415.

While a wavelet transform method is preferred for determining a match score, it is recognized that other signal processing methods for determining one or more salient feature of an EGM signal may be used which allow morphological comparisons to be made between two stored snapshots. An appropriate match metric may then be computed based on the equivalence of these salient features. For example, other morphology comparison methods may include QRS width determination as described in the Mader '441 patent; point-by-point comparisons for digitized waveform data resulting in a morphology index value as generally disclosed in U.S. Pat. No. 5,447,519 issued to Peterson; template matching by signature analysis as described in U.S. Pat. No. 5,273,049 issued to Steinhaus et al.; or conversion to discrete digital signals as described in U.S. Pat. No. 5,718,242 issued to McClure et al., each of which patents are incorporated herein by reference in their entirety.

At step 420, a temporary SVT template is derived from the stored QRS snapshots. A temporary SVT template is generated based on the QRS snapshot having the highest matching score sum, i.e., the QRS snapshot that most closely resembles all of the other QRS snapshots for a given episode. Alternatively, a temporary SVT template may be generated by averaging two or more QRS snapshots having higher matching score sums for a given episode.

The temporary SVT template may optionally be required to match a minimum number of other snapshots for a given episode before being stored as a provisional SVT template. At step 425, the temporary SVT template derived at step 420 is required to match at least X other QRS snapshots stored for the current episode, for example at least 3 other QRS snapshots, before the temporary SVT template is stored as a provisional SVT template at step 435. If the temporary SVT template does not meet the criteria set for matching a minimum number of the other QRS snapshots from the same episode, a provisional SVT template is not created as indicated at step 430. No SVT template is created when the comparisons between the snapshots reveal changes in the EGM morphology between the collected QRS snapshots. Such changes may be indicative of a polymorphic VT or VF.

Alternatively, particularly in circumstances where no QRS snapshots match, a nominal temporary SVT template may be generated from any one or more of the QRS snapshots stored during a single episode and stored as a nominal provisional template at step 430. Steps 410 through 435 for creating a provisional SVT template may be repeated for each arrhythmia episode for which stored QRS snapshots are available.

If a provisional SVT template is created at step 435, the episode from which the QRS snapshots were obtained for creating the provisional template should be verified as an actual SVT episode. Step 440 will generally require manual confirmation by a clinician that the episode from which the provisional SVT template was generated is actually an SVT and not a true VT/VF. The clinician may thereafter activate the confirmed SVT template for use in arrhythmia discrimination schemes, as will be described in greater detail below, by confirming the provisional template at step 445. A confirmed SVT template may be updated at any time based on new arrhythmia episode data by repeating method 400.

Step 445 may require only a positive confirmation by the clinician that the provisional SVT template was generated by one or more QRS snapshots obtained during a valid SVT episode, and that the confirmed SVT template should be used for future arrhythmia discrimination. However, step 445 may optionally include a retrospective analysis of stored episodes to verify the accuracy and specificity of rhythm discrimination using the provisional SVT template for morphological analysis.

Figure 4:
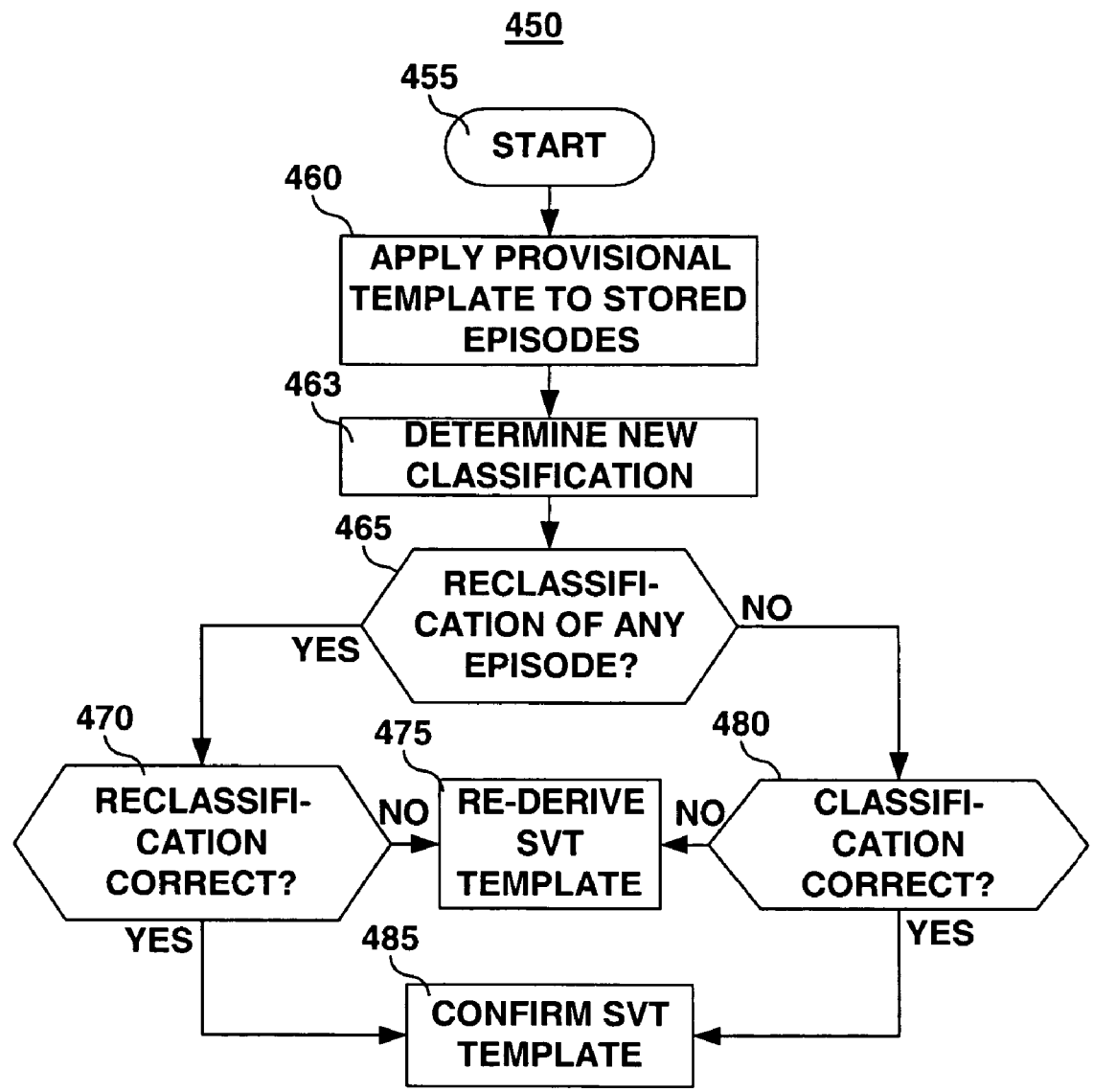
FIG. 4 is a flow chart summarizing steps included in one embodiment of the present invention for confirming a provisional template as a permanent SVT template.

Method 450 shown in FIG. 4 summarizes steps included in one embodiment of the present invention for confirming a provisional template as an SVT template. Method 450 is initiated at step 455 upon a command by a physician or other user. At step 460 the provisional template is applied to the stored snapshots of any stored arrhythmia episodes for rhythm discrimination purposes according to software or firmware/hardware implemented algorithms. Method 450 will normally be executed offline by external device 350 using actual stored arrhythmia episode data retrieved from device 10. The methods for classifying an arrhythmia based on the use of an SVT template will be described in greater detail below. Generally, the same morphology comparison methods utilized for determining match scores as described previously may be used for determining if the morphology of a stored QRS snapshot from a previously classified arrhythmia episode matches the provisional SVT template. Criteria based on the number of QRS snapshots matching the provisional SVT template are used in determining a new rhythm classification at step 463 for each stored episode.

At decision step 465, a determination is made as to whether any stored episode has been re-classified, i.e., the new classification determined at step 463 does not agree with the original classification of the stored episode. Any reclassified episodes are preferably marked and displayed on external device 350. If any reclassifications have been made, verification by a clinician or other user that the reclassification is correct is performed at step 470. If the reclassification(s) are incorrect, a provisional SVT template may be redetermined according to method 400 described above using a different episode of stored QRS snapshots. If the reclassification is correct, the provisional SVT template may be confirmed as an SVT template at step 485 and may then be activated for use in arrhythmia discrimination methods from that point on.

Likewise, if no reclassifications were made, as determined at decision step 465, but all original classifications were correct, the SVT template may be confirmed at step 485. If the original classification(s) were incorrect, as determined at decision step 480, and application of the provisional SVT template did not result in a corrected reclassification, a new provisional SVT template may be derived at step 475 according to method 400. Thus, method 450 may be executed to provide assurance that a selected provisional SVT template will improve the accuracy and specificity of arrhythmia episode classifications.

In accordance with a preferred embodiment of the present invention, morphological information is stored by the implantable device along with other arrhythmia episode information and retrieved from the implanted device for display on a graphical user interface. Implantable cardioverter defibrillator devices customarily store information relating to detected arrhythmia episodes such as the arrhythmia classification made, the date, time and duration of the detection, whether or not a therapy was delivered and was successful, and an EGM segment of the episode. However, morphological information has heretofore not been displayed in such episode reports. When morphology analysis methods are utilized for making an arrhythmia detection, it is desirable to include morphology-related information with other episode data.

Figure 5:
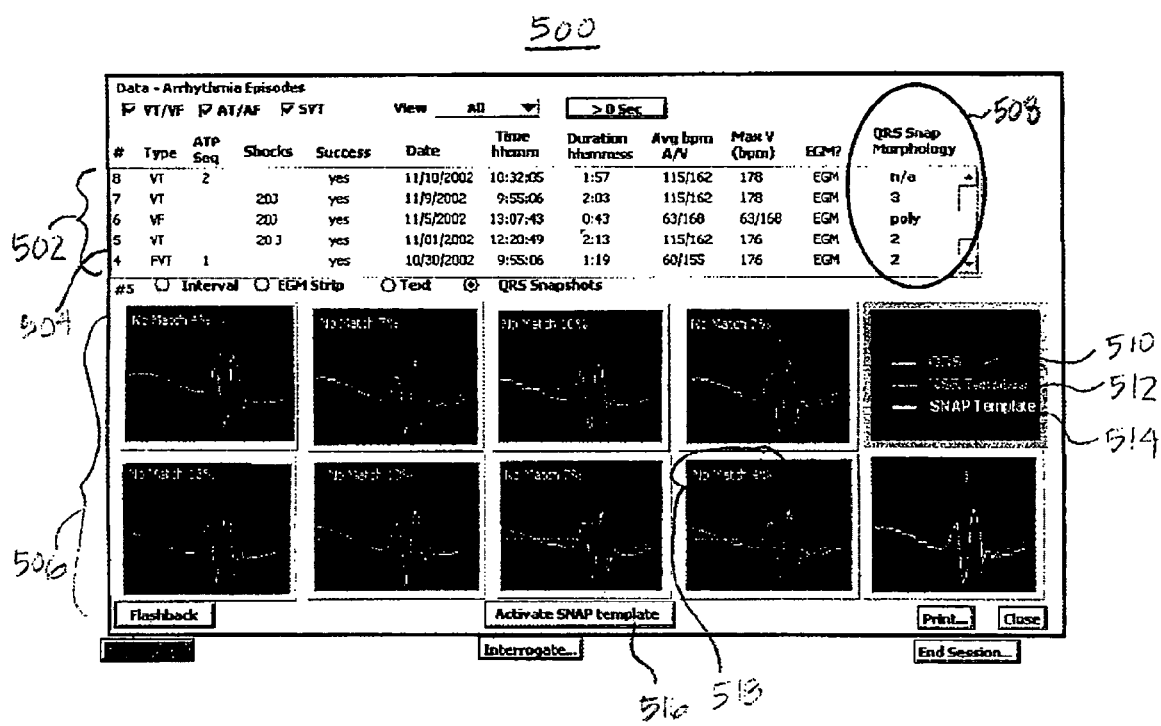
FIG. 5 is an illustration of one embodiment of a graphical user interface (GUI) including morphology-related information with arrhythmia episode data.

FIG. 5 is an illustration of one embodiment of a graphical user interface (GUI) including morphology-related information. An application program stored in the memory 354 of external device 350 may be executed by processor 354 to retrieve and display data received from the implanted device 10. The presentation of data as it might appear to a clinician on display 354 is shown in FIG. 5.

Generally ICD 10 has recorded a series of arrhythmia episodes and this series of events is displayed in window 502. An event 504 may be selected using the user interface 354 which may be a keyboard or other pointing device. Once an event 504 is selected, graphical representations of QRS snapshots recorded by device 10 during the event 504 may be presented in a second window 506. For example, in the embodiment shown 8 QRS snapshots are displayed.

The GUI 500 illustrated in FIG. 5 may be embodied in a system for controllably displaying information retrieved from an implanted device as generally described in U.S. Pat. No. 6,583,796 to Jamar, et al., incorporated herein by reference in its entirety. Other systems for displaying data obtained from an implantable device in which the present invention may be implemented are disclosed in U.S. Pat. No. 6,473,638 issued to Ferek-Petric, U.S. Pat. No. 5,722,999 issued to Snell, and U.S. Pat. No. 5,833,623 issued to Mann et al., all of which patents are hereby incorporated herein by reference in their entireties.

As shown in FIG. 5, a data column 508 in window 502 displays data relating to EGM morphology. For example, in the embodiment shown, a morphology index assigned to the QRS snapshot morphology, which may correspond to a provisional SVT template, is displayed. A method for determining a morphology index for a QRS snapshot morphology will be described in greater detail below. The morphology index may be used to identify events having SVT template morphologies of substantially equivalent morphology by assigning the same morphology index to those events. Events having SVT template morphologies that have changed compared to previous SVT templates may be differentiated by assigning a new morphology index. In other embodiments, displayed morphology-related information may include the value of an EGM morphology metric determined for a given episode which may be a salient feature of the EGM signal such as QRS width or a wavelet transform coefficient. Displayed morphology-related information may alternatively or additionally include a morphology match metric indicating the agreement between QRS snapshots acquired during a given event with a template.

As indicated previously, upon selecting a particular event 504, the corresponding QRS snapshots are displayed in individual panels in window 506. Each QRS snapshot 510 may be graphically displayed with an overlying QRS snapshot template (SNAP template) 514 created from stored snapshots which may correspond to a provisional or permanent SVT template. If a normal sinus rhythm (NSR) template 512 has also been established, the NSR template 512 may also be displayed simultaneously with a QRS snapshot 510 and a QRS snapshot template 514 to allow visual comparison of a given QRS signal and morphology templates 512 and 514 that may be selected or have already been activated for use in discriminating arrhythmias. As shown in GUI 500, a match metric 513 may be displayed corresponding to each QRS snapshot display indicating the result of a comparative analysis between the QRS snapshot and one or more reference templates 512 and 514.

GUI 500 is designed to ease the burden on a clinician in selecting a provisional SVT template and verifying it as a permanent SVT template. For example, provisional SVT templates may be created for each arrhythmia episode for which QRS snapshots are available from which derived temporary templates meet predetermined matching criteria. By providing a morphology index, a physician may select critical events having a changed QRS snapshot morphology for examining first for verification as a permanent SVT template. Stored episodes are typically displayed in a chronological order, but, by applying a morphology index to each episode, stored episodes may sorted, grouped, and displayed according to a morphology index or other morphology metric. By displaying stored arrhythmia events according to morphological groupings, a clinician or other user is able to quickly identify templates associated with a changed morphology that may be of interest.

In the example shown in FIG. 5, episode number 7 having a QRS snapshot morphology assigned an index value of 3 may be selected first as a provisional SVT template to be examined for verification as a permanent SVT template as described previously. Once a provisional SVT template is selected and verified, it may be activated by a user as a permanent SVT template for use in arrhythmia discrimination methods to be described below by using the "Activate SNAP template" button 516.

Figure 6:
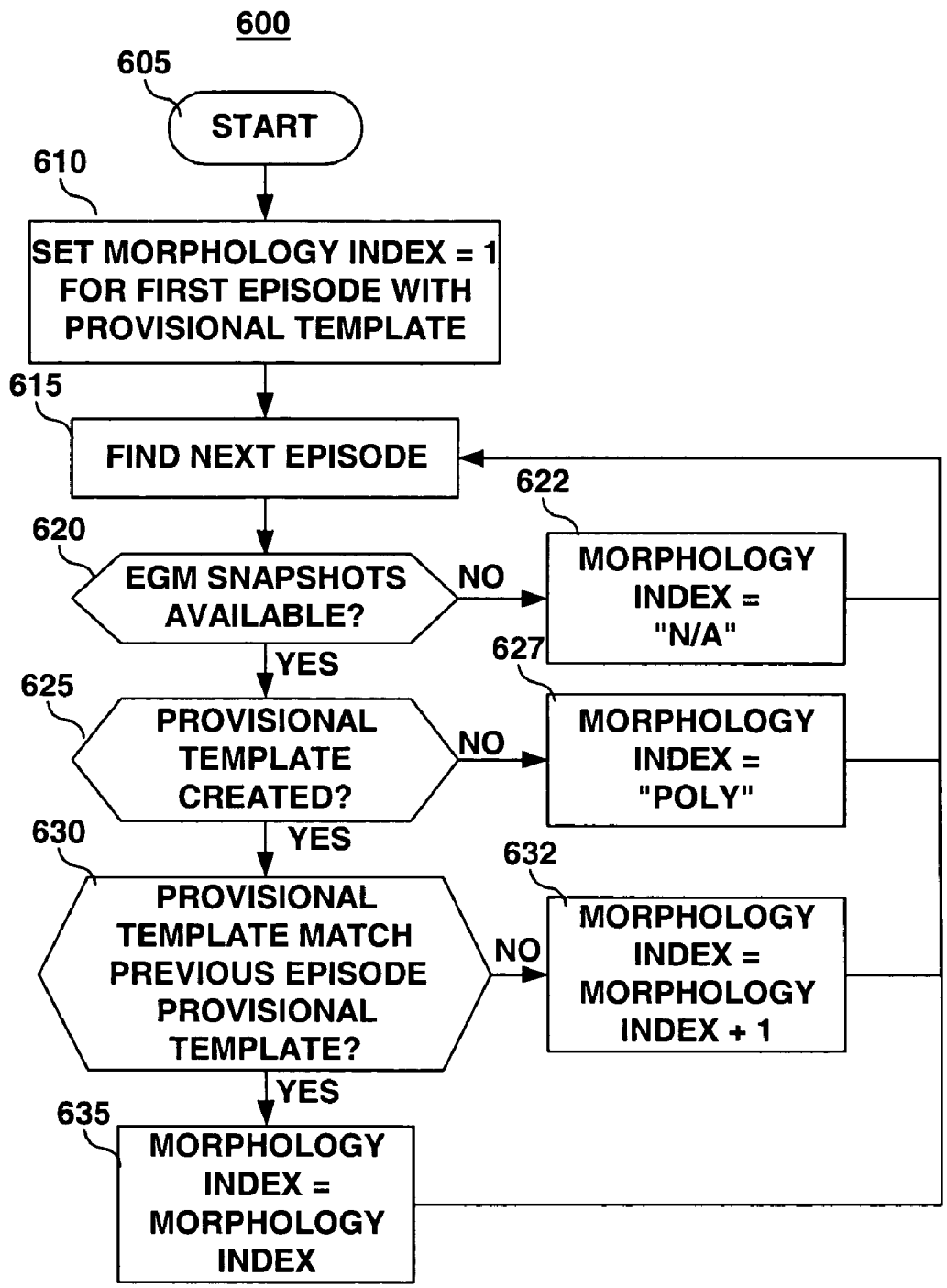
FIG. 6 is a flow chart summarizing steps included in one embodiment of the present invention for determining a morphology index for displaying in the GUI shown in FIG. 5.

FIG. 6 is a flow chart summarizing steps included in one embodiment of the present invention for determining a morphology index for displaying in GUI 500 as shown in FIG. 5. Method 600 is initiated at step 605, and the earliest stored arrhythmia episode for which a provisional template was created is identified at step 610. Method 600 may be initiated manually by a user, automatically by external device 350 upon data retrieval, or by microprocessor 224 of device 10 when episode data is logged to memory.

The morphology index for the earliest provisional template created is set equal to 1 at step 610. At step 615, the next stored episode is identified, and at decision step 620 the method 600 determines whether QRS snapshots were stored for that episode. If no QRS snapshots are available, the rate may have been too fast to acquire QRS snapshots making the morphology index indeterminable. The morphology index is assigned a value or label indicating that it is not applicable ("n/a") to the current episode at step 622.

If QRS snapshots are available, as determined at decision step 620, method 600 determines if a provisional SVT template was created at decision step 625 for the current episode. If not, the morphology index is assigned a value or label indicating a polymorphic rhythm at step 627. An episode for which QRS snapshots are available but creation of a provisional SVT template failed indicates that the temporary template did not meet matching critieria as described previously in conjunction with method 400 of FIG. 3. Changing QRS morphology evidences a polymorphic rhythm. In an alternative embodiment, the number of snapshots for an episode matching a temporary SVT template may be displayed.

If a provisional SVT template has been created, as determined at decision step 625, the provisional template for the current episode is compared at decision step 630 to the most recent provisional SVT template created prior to the current episode. If the provisional templates match, the morphology index for the current episode is assigned a morphology index at step 635 equal to the previous morphology index value, indicating the provisional template morphology for the current episode is substantially equal to the previous provisional template morphology.

If, however, the provisional template for the current episode does not match the most recent prior provisional template, as determined at decision step 630, the morphology index is increased by a value of 1 such that the current episode is assigned a new morphology index value. The new morphology index value indicates that the provisional template for the current episode is different than the previous provisional template.

After assigning one of the possible morphology index values to the current stored arrhythmia episode, at one of steps 622, 627, 632 or 635, method 600 returns to step 615 to identify the next stored arrhythmia episode and to assign a morphology index. The morphology indices assigned to each stored episode may then be displayed on GUI 500 as described previously.

Figure 7:
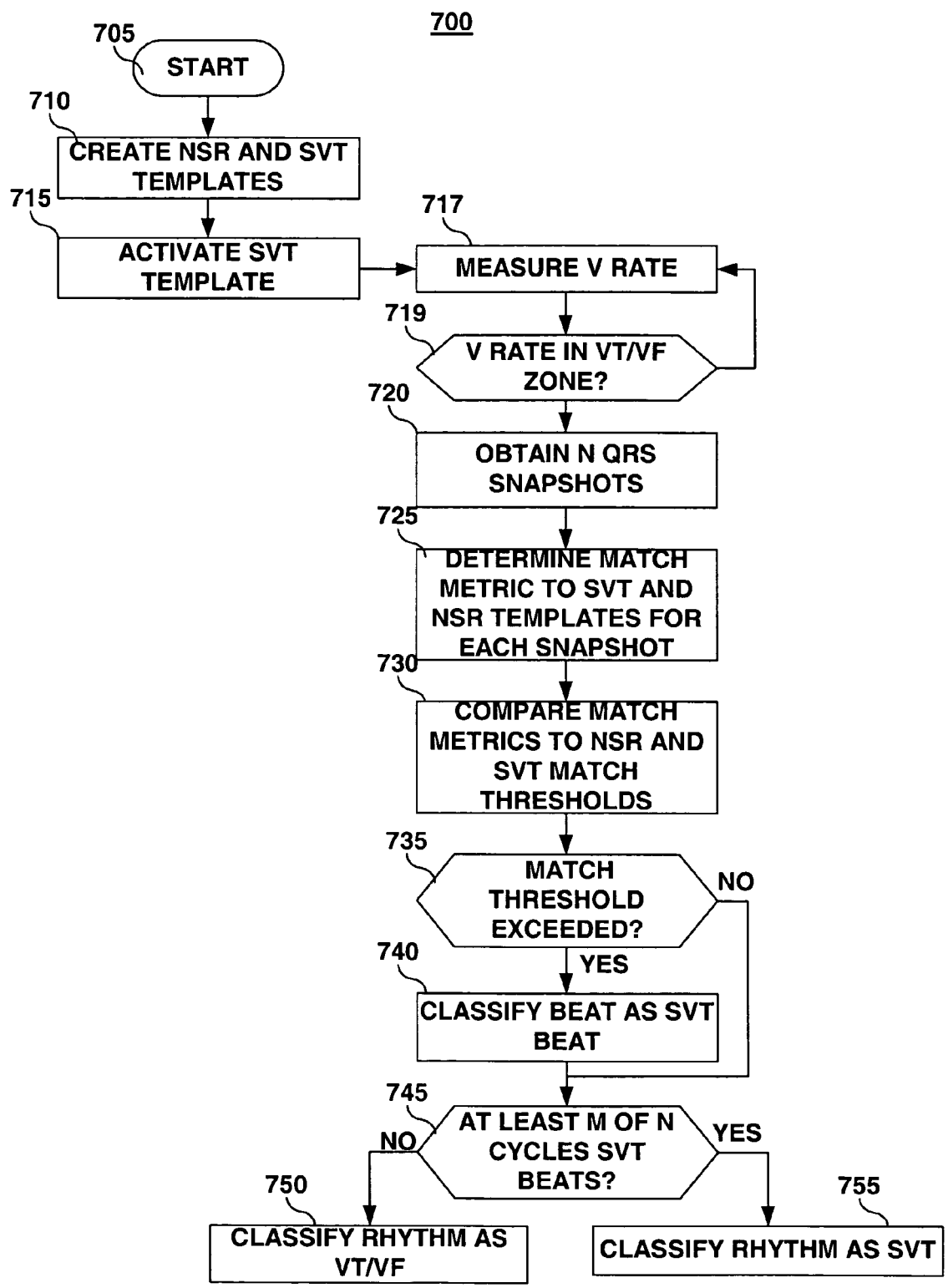
FIG. 7 is a flow chart summarizing steps included in a method for discriminating SVT from VT/VF using an SVT template generated according to the present invention.

Once a provisional SVT template is created, verified and activated as a confirmed SVT template, it is available for use in discriminating SVT from VT/VF during a fast ventricular rate that meets VT/VF rate-based detection criteria. FIG. 7 is a flow chart summarizing steps included in a method for discriminating SVT from VT/VF using an SVT template generated according to the present invention. Method 700 is initiated at step 705 when morphology discrimination methods are enabled by a user. At step 710, an SVT template is created according to method 400 described previously. The SVT template is activated by a user at step 715. In addition to the SVT template, a NSR template may be created at step 710. A NSR template may be created according methods described in the above-incorporated '316 patent to Gillberg, or as described in either of commonly assigned U.S. patent application Ser. No. 10/132,773, entitled "Automated Template Generation Algorithm For Implantable Device" to Koyrakh et al. and U.S. patent application Ser. No. 09/995,176, entitled "Automated Template Generation Algorithm For Implantable Device" to Koyrakh et al., both incorporated herein by reference in their entireties. A NSR template may be created automatically any time during a regular, slow ventricular rate and may be updated periodically during normal ventricular rates.

At step 717, upon sensing an R-wave, the ventricular rate is measured. If the ventricular rate is in a VT/VF detection zone or other rate zone for which morphology analysis is triggered, QRS snapshots are obtained at step 720. An added criteria for triggering morphology analysis may require that the ventricular rate is less than a specified SVT upper rate limit, above which ventricular rates are considered too fast to be the result of an SVT. If the ventricular rate is not in the VT/VF zone or at a rate less than a rate for triggering morphology analysis, method 700 returns to step 717 to continue monitoring the ventricular rate. It is recognized that a VF detection may be made in response to a ventricular rate in a VF zone and greater than an SVT upper rate limit, which is a rate greater than the rate zone in which morphology analysis is applied for SVT discrimination. Furthermore, in alternative embodiments, QRS snapshot acquisition and morphology analysis may not be limited to occur upon fast ventricular rate-related trigger criteria. QRS snapshot acquisition and morphology analysis may be performed continuously or on a periodic basis as part of an arrhythmia detection and classification scheme.

A number of QRS snapshots are obtained at step 720, and each snapshot is compared to the SVT template and the NSR template at step 725 for determining a match metric. Preferably a match metric is determined as a match score for each comparison as described in the '316 patent to Gillberg. The match score or other match metric for each comparison is compared to a match threshold at step 730. A unique match threshold may be defined for each of NSR template matching and SVT template matching. If the match score between a QRS snapshot and either the NSR or SVT templates exceeds the respective match threshold as determined at decision step 735, the beat is classified as an SVT beat at step 740. If neither match threshold is exceeded, the beat may be considered a VT/VF beat.

At decision step 745, method 700 determines if an SVT detection criteria is met. An SVT detection criteria may require, for example, that at least a given number M out of N QRS snapshots must be classified as SVT beats at step 740. For example, at least 3 out of 8 QRS snapshots must have match scores that exceed a NSR or SVT template match threshold. If this criteria is met at decision step 745, the rhythm is classified as an SVT at step 755. If less than M QRS snapshots out of N snapshots exceed a NSR or SVT template match threshold, the rhythm is classified as VT/VF at step 750 as long as any other required rate-based or other criteria for VT/VF detection are met.

The classification of VT/VF or SVT made at steps 750 or 755, respectively, may be used for selecting an appropriate arrhythmia therapy according to normal device operations. The episode may be stored in device memory with the QRS snapshots and related morphology information for later retrieval and display on a GUI as described previously.

Thus, a system and associated methods have been described for creating SVT templates, utilizing such SVT templates in morphology-based rhythm discrimination, and reporting morphology-related information with arrhythmia episode data. The present invention has been described in detail herein according to preferred embodiments contemplated to date. It is recognized that one having skill in the art and the benefit of the teachings provided herein may conceive of numerous modifications or variations of the described embodiments.

The descriptions provide herein are intended to be exemplary, therefore, and not limiting with regard to the following claims.

What is claimed is:

1. A method of discriminating cardiac depolarizations, comprising:
   detecting indications of a plurality of indications associated with determining the presence of a first event, the plurality of indications occurring at a rate corresponding to the first event;
   storing, prior to detecting all of the plurality of indications, a plurality of segments corresponding to signals associated with the detected indications occurring at a rate corresponding to the first event;
   comparing the plurality of segments; and
   generating, in response to the comparing, a template for distinguishing the first event from a second event different from the first event and corresponding to the rate corresponding to the first event.

2. The method of claim 1, wherein generating a template comprises determining whether a segment of the plurality of segments matches a predetermined number of the plurality of segments.

3. The method of claim 1, further comprising:
   comparing the generated template with a segment corresponding to a previously classified arrhythmia episode;
   updating the generated template in response to the comparing of the generated template.

4. The method of claim 3, further comprising displaying information corresponding to the generating.

5. The method of claim 4, wherein displaying comprises:
   displaying the plurality of segments; and
   displaying a match metric corresponding to each of the displayed plurality of segments in response to a comparative analysis between the plurality of segments and one or more reference templates.

6. The method of claim 1, further comprising:
   setting a first index associated with a first generated template;
   comparing a second generated template generated subsequent to the first generated template to the first generated template;
   setting a second index associated with the second generated template in response to the comparing of the second generated template.

7. The method of claim 6, further comprising displaying the first index and the second index.

8. The method of claim 7, further comprising:
   displaying the plurality of segments; and
   displaying a match metric corresponding to each of the displayed plurality of segments in response to a comparative analysis between the plurality of segments and one or more reference templates.

9. The method of claim 1, further comprising:
   determining the presence of the first event;
   comparing a second plurality of segments corresponding to first depolarizations occurring subsequent to determining the presence of the first event to the generated template; and
   classifying the first depolarizations as one of the first event and the second event in response to comparing the second plurality of segments.

10. The method of claim 1, wherein the first event is one of ventricular tachycardia and ventricular fibrillation and the second event is a supraventricular event.

* * * * *